United States Patent [19]

Müllner et al.

[11] Patent Number: 5,268,272
[45] Date of Patent: Dec. 7, 1993

[54] COMPLEXES CONTAINING GLYCOSYL-PHOSPHATIDYLINOSITOL PROTEINS AND CHOLANIC ACID DERIVATIVES, A PROCESS FOR THEIR PREPARATION AND THEIR USE

[75] Inventors: Stefan Müllner, Hochheim am Main; Günter Müller, Sulzbach/Taunus, both of Fed. Rep. of Germany

[73] Assignee: Hoechst Aktiengesellschaft, Frankfurt am Main, Fed. Rep. of Germany

[21] Appl. No.: 22,317

[22] Filed: Feb. 25, 1993

[30] Foreign Application Priority Data

Feb. 29, 1992 [DE] Fed. Rep. of Germany ....... 4206395

[51] Int. Cl.$^5$ .................. C07K 15/06; A61K 37/02; C12P 21/00
[52] U.S. Cl. .................................... 435/52; 435/68.1; 435/188; 530/350; 530/352; 530/813; 530/827
[58] Field of Search ............... 435/188, 68.1, 52; 530/352, 813, 827, 350

[56] References Cited

U.S. PATENT DOCUMENTS

| | | | |
|---|---|---|---|
| 4,359,529 | 11/1982 | Tsuji et al. | 435/52 |
| 4,375,431 | 3/1983 | Bradford et al. | 435/68.1 |
| 4,783,402 | 11/1988 | Kokusho et al. | 435/52 |
| 4,977,091 | 12/1990 | Gilmanov et al. | 435/271 |

FOREIGN PATENT DOCUMENTS 532915  3/1993  European Pat. Off. .
3623747  1/1988  Fed. Rep. of Germany .

*Primary Examiner*—Herbert J. Lilling
*Attorney, Agent, or Firm*—Finnegan, Henderson, Farabow, Garrett & Dunner

[57] ABSTRACT

Complexes which contain at least one glycosyl-phosphatidylinositol protein and at least one cholanic acid derivative of the formula I

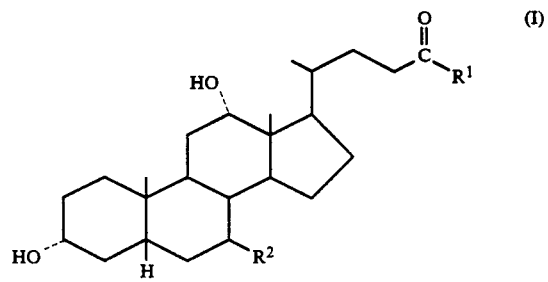

are suitable, inter alia, in enzyme tests and as aids in chemical reactions; where $R^1$ is —NH—CH$_2$—CH$_2$—SO$_3$ or —NH—CH$_2$—COOH, $R^2$ is NR$^3$R$^4$ or —OR$^5$; $R^3$, $R^4$ or $R^5$ are a hydrogen atom, (C$_1$–C$_5$)-alkyl, (C$_3$–C$_6$)-cycloalkyl, substituted acetyl, halogen, succinyl, substituted benzyl or substituted benzoyl.

6 Claims, No Drawings

COMPLEXES CONTAINING GLYCOSYL-PHOSPHATIDYLINOSITOL PROTEINS AND CHOLANIC ACID DERIVATIVES, A PROCESS FOR THEIR PREPARATION AND THEIR USE

Description

Integral membrane proteins which are embedded in the lipid double layer by one or more sections of the polypeptide chain are in the main water-insoluble and can only be converted into a water-soluble form, while preserving their structure, by solubilizers, so-called detergents.

Also known (DE 36 23 747) among the multiplicity of possible detergents are cholanic acid derivatives, with which some membrane proteins can be converted into a water-soluble form. It is further known that these cholanic acid derivatives preferably convert proteins from plasma membranes into a water-soluble form (solubilize). Thus far there is no known selectivity for particular membrane proteins.

For some time, a class of membrane proteins has been known which are bound covalently by a glycosylphosphatidylinositol anchor to the plasma membranes (G. A. M. Cross (1987) Cell 48, pp. 179-181; M. G. Low (1987) Biochem. J. 244, 1-13). Solubilization of these membrane proteins, e.g. alkaline phosphatases in functional form, has hitherto only been achieved by treatment with protease, such as trypsin or papain, or following release by bacterial phospholipase-C (I. F. Thompson et al. (1987) Biochem. Biophys. Res. Commun. 145, 118-125). In this case, though, only the hydrophilic moiety of the membrane proteins is obtained. However, for structural and functional studies, the amphipathic form, with an intact membrane anchor, should be present. Membrane proteins with glycosyl-phosphatidylinositol anchors (GPI proteins) can be solubilized with conventional detergents only in association with other membrane proteins. For this, n-butanol too is often employed in the extraction (A. S. Malik and M. G. Low (1986) Biochem. J. 240, pp. 519-527). However, in this form of extraction, the original spatial structure of these membrane proteins can frequently be lost. This is manifested, for example, in reduced accessibility of the GPI-membrane anchor for cleavage by GPI-specific phospholipases.

It has now been found that GPI proteins essentially retain their original spatial structure, as well as their activity and function, if they are gently converted into a water-soluble form from the cell membrane using cholanic acid derivatives. These water-soluble complexes obtained in this way can be cleaved, selectively and in high yield, by phospholipases into a phosphoinositol-glycan-protein moiety and diacylglycerol. Additionally, the glycosyl-phosphatidylinositol proteins (GPI proteins) can be selectively separated from other membrane proteins using the cholanic acid derivatives.

The invention therefore relates to water-soluble complexes containing at least one glycosyl-phosphatidylinositol protein and at least one cholanic acid derivative.

The water-soluble complexes according to the invention have the property that they form sedimentable aggregates in aqueous solution at neutral pH only if they are rotated in a centrifuge for 30 minutes at more than 100,000 times gravitational acceleration (g).

The cholanic acid derivatives are compounds of the formula I

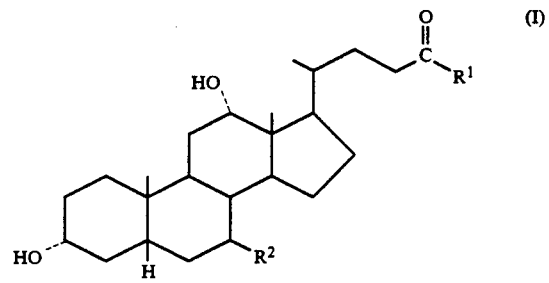

and/or physiologically tolerated salts of the compound of the formula I; in which the symbols $R^1$ and $R^2$ have the following meaning:

$R^1$ is:
a) $-NH-CH_2-CH_2-SO_3$ or
b) $-NH-CH_2-COOH$, $R^2$ is:

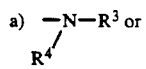

b) $-O-R^5$, where $R^3$, $R^4$ or $R^5$ are identical or different and have, independently of each other, the following meaning:
1) hydrogen atom,
2) ($C_1-C_5$)-alkyl, straight-chain or branched,
3) ($C_3-C_6$)-cycloalkyl,
4) acetyl,
5) acetyl, monosubstituted or polysubstituted by 5.1 halogen such as fluorine, chlorine or bromine,
6) halogen such as fluorine, chlorine or bromine,
7) succinyl,
8) benzoyl, monosubstituted or polysubstituted by
8.1 hydrogen atom
8.2 $-NO_2$,
8.3 $-N_3$,
8.4 $-NCS$,
8.5 $-NH_2$,
8.6 $-N(R^7)_2$,
where $R^7$ has the meaning of b 1) to b 7) or
8.7 halogen such as fluorine, chlorine or bromine or
9) benzyl, monosubstituted or polysubstituted by the radicals named in b 8.1 to b 8.7.

Preferred are compounds of the formula I; in which
$R^1$ is $-NH-CH_2-CH_2-SO_3$ and
$R^2$ is $-NHR^4$,
where $R^4$ has the following meaning:
a) ($C_1-C_5$)-alkyl,
b) benzoyl, monosubstituted or polysubstituted by
1) hydrogen atom,
2) $NO_2$,
3) $NH_2$ or
4) halogen such as fluorine, chlorine or bromine or
c) benzyl, monosubstituted or polysubstituted by the radicals named in b 1) to b 4).

Particularly preferred are compounds of the formula I; in which
$R^1$ is $-NH-CH_2-CH_2-SO_3$ and $R^2$ is $-NH-R^4$, where $R^4$ has the following meaning:
a) benzoyl or
b) benzoyl substituted by $NH_2$.

Very particularly preferred as the cholanic acid derivative is 4'-amino-7-benzamido-3α,12α-5β-taurocholic acid.

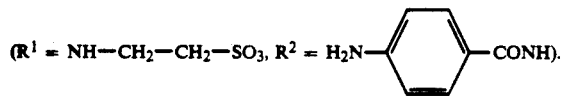

($R^1 = NH-CH_2-CH_2-SO_3$, $R^2 = H_2N-\langle\text{phenyl}\rangle-CONH$).

Suitable physiologically tolerated salts of the cholanic acid derivatives according to the invention are, for example, alkali metal, alkaline earth metal or ammonium salts, as well as salts with physiologically tolerated organic ammonium or triethylamine bases. The term glycosyl-phosphatidylositol proteins (GPI proteins) is understood to mean compounds which are anchored by their glycosyl-phosphatidylinositol moiety in a cell membrane of microorganisms, plant cells, fungal cells or animal cells and possess a protein moiety. Examples of GPI proteins are 5'-nucleotidase, alkaline phosphatase and acetylcholinesterase.

The abovementioned cholic acid derivatives can be prepared by methods known from the literature (DE 36 23 747).

To prepare 7-amino-cholic acid, for example cholic acid is oxidized in the 7 position according to Fieser and Rajagopolan (JACS 71, 3935), converted to the oxime according to Redel et al. (Bull. Soc. Chin. Fr. 1949, p. 877), conjugated with taurine according to Tserng et al. (J. Lipid Res. 18, 404, 1977) and subsequently hydrogenated to the amine under pressure on a platinum catalyst. The amine is subsequently coupled with nitroaryl alcohol or an aromatic nitro carboxylic acid, preferably 4-nitrobenzoic acid, with the addition of N-ethoxycarbonyl-2-ethoxy-1,2-dihydroquinoline (EEDQ) in dimethylformamide, and the 4-nitrobenzamide is hydrogenated to the amino compound, preferably to the 4-aminobenzoic acid derivative, in methanolic solution acidified with acetic acid and using $PtO_2xH_2O$ as catalyst.

The synthesis of the 3- and/or 7-hydroxy-taurocholic acid esters takes place in an analogous manner by reacting the corresponding hydroxy compound with a nitroaryl alcohol or an aromatic nitro carboxylic acid, preferably 4-nitrobenzoic acid, with the addition of EEDQ in DMF. Subsequently, as described, the compound is hydrogenated on a $PtO_2$ catalyst.

Preparation of the water-soluble complexes according to the invention takes place for example by
a) isolating membranes which contain GPI proteins,
b) incubating the membranes with at least one cholanic acid derivative and
c) isolating water-soluble complexes containing at least one GPI protein and at least one cholanic acid derivative.

GPI proteins can be obtained from numerous organisms, for example from rats, pigs or cattle. For example, plasma membranes from rat adipocytes are suitable for obtaining 5'-nucleotidase and membranes from bovine erythrocytes for obtaining acetylcholinesterase.

In process step a), the best procedure is as follows: membranes which contain GPI proteins are isolated by, for example, separating out adipocytes from rat epididymal adipose tissue by collagenase digestion (J. Gliemann, Diabetologia, 1967, 3, pp. 382-388). The isolated cells are disintegrated in an homogenizer, and the plasma membranes are concentrated by differential centrifugation and subsequently purified by sucrose gradient centrifugation (15 to 40% sucrose) (D. W. McKeel and L. Jarret, J. Cell. Biol., 1970, 44, pp. 417-432).

In process step b), the best procedure is to incubate the isolated membranes with a cholanic acid derivative, for example 4'-amino-7β-benzamido-3α,12α,5β-taurocholic acid (BATC). The concentration of the cholanic acid derivatives is about 0.01 to 0.5%, preferably 0.02 to 0.2%, particularly preferably 0.05 to 0.1%. The temperature is from 0° C. to 40° C., preferably 0° C. to 15° C. The incubation time is from 10 min to 2 hours, preferably 15 min to 1 hour, very particularly preferably 20 min to 40 min.

In process step c), the best procedure is to centrifuge the reaction mixture obtained in step b) at 35,000 to 150,000×g, preferably 50,000 to 100,000×g. One or more centrifugations may be carried out; the centrifugal acceleration during one centrifugation step may be the same or may vary. The centrifugal acceleration in a plurality of centrifugations may be the same or may be different. The centrifugation time may vary over a wide range; centrifugation times of 15 min up to 3 hours, preferably 30 min to 1 hour, have proven favorable. The water-soluble complexes according to the invention are present in the supernatant following the centrifugation step. They can be used as such in solution, or optionally frozen or further purified. Appropriate methods are known from the literature, for example:

Brodbeck, U.; Gentinetta, R.; Ott, P. (1981) in "Membrane Proteins" (Azzi A., Brodbeck U., Zahler P. eds.) Springer-Verlag, Berlin, 85-96. Stieger, S.; Brodbeck, U. (1985), J. Neurochem. 44, 48-56; Butikofer, P.; Kuypers, F. A.; Shackleton, C.; Brodbeck, U., Stieger, S. (1990), J. Biol. Chem. 265, 18983-18987. Ott, P.; Jenny, B.; Brodbeck, U. (1975), Eur. J. Biochem 57, 469-480.

The water-soluble complexes thus obtained are suitable, for example, in enzyme tests, for the qualitative or quantitative determination of substrates in chemical syntheses or for stabilization of test systems in each of which GPI proteins are present, and for purifying GPI proteins.

The invention further relates to a process for selectively preparing the water-soluble complexes according to the invention. The abovementioned preparation of the water-soluble complexes is distinguished by a high selectivity of the cholanic acid derivatives for the GPI proteins. Other detergents, such as octyl glucoside or Triton X-100, exhibit a significantly inferior selectivity for the GPI proteins.

The percent values in the following examples relate in each case to percent by volume, unless otherwise indicated.

EXAMPLE 1

Water-soluble 5'-nucleotidase-BATC complex
a) Adipocytes are isolated from rat epididymal adipose tissue by collagenase digestion (according to J. Gliemann (1967) Diabetologia 3, pp. 382-388), washed and homogenized in a glass homogenizer (B. Braun, Melsungen AG, Apparatebau). After differential centrifugation of the homogenate (5 minutes at 1000×g and subsequently 20 min at 16,000×g), the resulting plasma membrane pellet is suspended in an aqueous 25 mM Tris/HCl buffer (pH 7.4, 250 mM sucrose, 1 mM EDTA) and purified by sucrose gradient centrifugation (linear gradient of 15–40% sucrose in 25 mM Tris/HCl) (D. W. McKeel and L. Jarrett (1970) J. Cell. Biol. 44, pp. 417–432).

b) The plasma membranes from a) are incubated with 0.1% 4'-amino-7β-benzamido-3α,12α,5β-taurocholic acid (BATC). The reaction time is 30 min at 4° C.

c) The incubation mixture from b) is centrifuged for 30 min at 150,000×g, the sedimented plasma membranes are discarded and the supernatant is subsequently centrifuged twice more for 30 min at 100,000×g and the sedimented membranes discarded on each occasion. The supernatant contains the water-soluble 5'-nucleotidase-BATC complex.

5'-Nucleotidase activity is demonstrated by hydrolysis of radioactive 5'-AMP. Following precipitation of the unhydrolyzed AMP by 0.3 N Ba(OH)$_2$, the radioactivity of the resulting adenosine is measured in the supernatant (according to E. M. Bailyes et al. (1982) Biochem. J. 203, pp. 245–251).

EXAMPLE 2

Water-soluble alkaline phosphatase-BATC complex

The preparation takes place as described in Example 1a) to 1c).

The alkaline phosphatase activity is determined spectroscopically by hydrolysis of p-nitrophenyl phosphate (Y. Ikehara et al. (1977) Biochim. Biophys. Acta 470, pp. 202–211).

EXAMPLE 3

Water-soluble acetylcholinesterase-BATC complex

Bovine erythrocytes (Sigma Chemie GmbH, Diesenhofen, Germany) are incubated as described in Example 1b) and 1c). For this, 1 mg of dried bovine erythrocytes are incubated in 1 ml of buffer (Tris/HCl, 25 mM, pH 7.4) with 0.1% BATC (based on the volume) at 4° C. for 30 min and subsequently centrifuged as in Example 1c).

The acetylcholinesterase (T. L. Rosenberry and D. M. Scoggin (1984) J. Biol. Chem. 259, pp. 5643–5652) is determined by hydrolysis of radioactive acetylcholine. The radioactivity of the liberated radioactive acetic acid is measured following removal of the unhydrolyzed radioactive acetylcholine by phase separation at acid pH.

EXAMPLE 4

Selective concentration of GPI proteins from cell membranes.

The selective concentration of GPI-anchored membrane proteins by BATC in comparison with detergents which are conventionally employed in membrane biochemistry takes place in the following way:

Bovine erythrocyte membranes and rat adipocyte plasma membranes (prepared as in Example 1a) or 3a)) are incubated in the presence of BATC (0.1%), octyl glucoside (0.5%) and Triton TX-100 (0.5%). After centrifugation (30 min, 100,000×g), the specific enzyme activities of the 5'-nucleotidase, alkaline phosphatase and acetylcholinesterase are determined in the supernatant and in each case calculated as a concentration factor with respect to the total specific activity in the detergent-solubilized incubation mixture before centrifugation. Table 1 shows the results

|                      | BATC 0.1% | octyl glycoside 0.5% concentration factor | Triton X-100 0.5% |
|----------------------|-----------|-------------------------------------------|-------------------|
| 5'-nucleotidase      | 4.4       | 1.5                                       | 1.0               |
| alkaline phosphatase | 3.5       | 1.2                                       | 0.8               |
| acetylcholinesterase | 4.8       | 1.6                                       | 0.9               |

EXAMPLE 5

Lipolytic cleavage of the GPI-protein 5'-nucleotidase

To demonstrate the efficient lipolytic cleavage of GPI proteins by bacterial PI(phosphatidylinositol)-specific phospholipases in the presence of BATC, rat adipocyte plasma membranes (Example 1) are incubated with PI-PLC (Bacillus cereus, Sigma Chemie GmbH) in the presence of 0.1% BATC, 0.5% deoxycholate or 0.1% Nonidet P-40.

Cleavage of the glycosyl-phosphatidylinositol membrane anchor of the 5'-nucleotidase by (G)PI-PLC(D) from Bacillus cereus is followed by the distribution behavior of the proteins (identified by their enzymatic activity) between a detergent (TX-114) phase and an aqueous phase. The amphiphilic membrane anchor-containing form accumulates in the detergent phase, the hydrophilic membrane anchor-free form is concentrated in the aqueous phase.

Phase separation with TX-114 takes place according to C. Bordier (1981) J. Biol. Chem. 256, pp. 1604–1607; J. G. Pryde and J. H. Phillips (1986) Biochem. J. 233, pp. 525–533; B. R. Ganong and J. P. Delmore (1991) Anal. Biochem. 193, pp. 35–37 with the following modifications: 1 ml of ice-cold TX-114 (2%) and 144 mM NaCl are added to 50 μl of incubation mixture. Phase separation is elicited by warming to 37° C. and centrifugation (2 min at 10,000×g). The detergent phase is re-extracted twice. The aqueous phases were combined. Table 2 shows the results:

|                       |            | Detergent       |              |
|-----------------------|------------|-----------------|--------------|
| Incubation time (min) | BATC 0.1%  | Nonidet P-40 0.1% | deoxycholate 0.5% |
| 0                     | 27         | 33              | 6            |
| 5                     | 55         | 48              | 8            |
| 30                    | 112        | 88              | 11           |
| 60                    | 256        | 211             | 19           |
| 90                    | 578        | 485             | 45           |
| 120                   | 732        | 654             | 109          |
| 240                   | 1842       | 1489            | 144          |
| 480                   | 2231       | 1651            | 162          |

In comparison with Nonidet P-40 or deoxycholate, lipolytic cleavage of the GPI-membrane anchors with (G)PI-PLCs in the presence of BATC (0.1%) takes place more rapidly and with markedly higher efficiency.

We claim:
1. A water-soluble complex containing at least one glycosyl-phosphatidylinositol protein and at least one cholanic acid derivative of the formula I

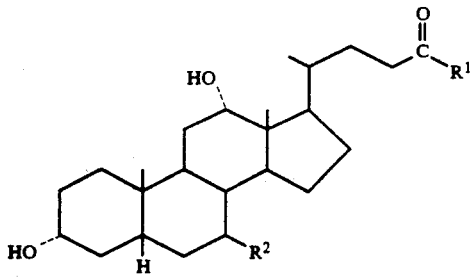

and/or physiologically tolerated salts of the compound of the formula I; in which the symbols $R^1$ and $R^2$ have the following meaning:

$R^1$ is:
a) —NH—CH$_2$—CH$_2$—SO$_3$ or
b) —NH—CH$_2$—COOH, $R^2$ is:

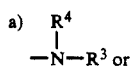

b) —O—R$^5$, where $R^3$, $R^4$ or $R^5$ are identical or different and have, independently of each other, the following meaning:
1) hydrogen atom,
2) (C$_1$-C$_5$)-alkyl, straight-chain or branched,
3) (C$_3$-C$_6$)-cycloalkyl,
4) acetyl,
5) acetyl, monosubstituted or polysubstituted by
   5.1 halogen such as fluorine, chlorine or bromine,
6) halogen such as fluorine, chlorine or bromine,
7) succinyl,
8) benzoyl, monosubstituted or polysubstituted by
8.1 hydrogen atom
8.2 —NO$_2$,
8.3 —N$_3$,
8.4 —NCS,
8.5 —NH$_2$,
8.6 —N(R$^7$)$_2$,
   where R$^7$ has the meaning of b 1) to b 4) or
8.7 halogen such as fluorine, chlorine or bromine or
9) benzyl, monosubstituted or polysubstituted by the radicals named in b 8.1 to b 8.7.

2. A water-soluble complex as claimed in claim 1, wherein
$R^1$ is —NH—CH$_2$—CH$_2$—SO$_3$ and
$R^2$ is —NHR$^4$, where R$^4$ has the following meaning:
a) (C$_1$-C$_5$)-alkyl,
b) benzoyl, monosubstituted or polysubstituted by
  1) hydrogen atom,
  2) NO$_2$,
  3) NH$_2$ or
  4) halogen such as fluorine, chlorine or bromine or
c) benzyl, monosubstituted or polysubstituted by the radicals named in b 1) to b 4).

3. A water-soluble complex as claimed in claim 1, wherein
$R^1$ is —NH—CH$_2$—CH$_2$—SO$_3$ and
$R^2$ is —NH—R$^4$, where R$^4$ has the following meaning:
a) benzoyl or
b) benzoyl substituted by NH$_2$.

4. A water-soluble complex as claimed in claim 1, which contains 4'-amino-7-benzamido-3α,12α,-5β-taurocholic acid as the cholanic acid derivative.

5. A water-soluble complex as claimed in claim 1, which contains 5'-nucleotidase, alkaline phosphatase or acetylcholinesterase as the glycosyl-phosphatidylinositol protein.

6. A process for preparing a water-soluble complex as claimed in claim 1, which comprises
a) isolating membranes which contain glycosyl-phosphatidylinositol proteins,
b) incubating the membranes with at least one cholanic acid derivative and
c) isolating a water-soluble complex containing at least one glycosyl-phosphatidylinositol protein and at least one cholanic acid derivative.

* * * * *